United States Patent
Song et al.

(10) Patent No.: US 8,868,182 B2
(45) Date of Patent: Oct. 21, 2014

(54) DEVICE BASED CARDIAC MONITORING AND STRESS TEST

(75) Inventors: Zhendong Song, Medina, MN (US); Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 178 days.

(21) Appl. No.: 13/549,983

(22) Filed: Jul. 16, 2012

(65) Prior Publication Data

US 2014/0018688 A1 Jan. 16, 2014

(51) Int. Cl.
*A61N 1/365* (2006.01)

(52) U.S. Cl.
USPC .................................. 607/9; 607/25; 600/517

(58) Field of Classification Search
None
See application file for complete search history.

(56) References Cited

U.S. PATENT DOCUMENTS

| | | | |
|---|---|---|---|
| 6,418,346 B1 | 7/2002 | Nelson | |
| 6,442,433 B1 | 8/2002 | Linberg | |
| 6,480,745 B2 | 11/2002 | Nelson | |
| 6,599,250 B2 | 7/2003 | Webb | |
| 7,734,346 B2 | 6/2010 | van Bolhuis | |
| 2004/0215242 A1 | 10/2004 | van Dalen | |
| 2005/0245975 A1 | 11/2005 | Hettrick | |
| 2006/0264767 A1 | 11/2006 | Shennib | |
| 2009/0281440 A1* | 11/2009 | Farazi et al. | 600/510 |
| 2011/0106195 A1* | 5/2011 | Kornet et al. | 607/14 |

* cited by examiner

*Primary Examiner* — Kennedy Schaetzle
(74) *Attorney, Agent, or Firm* — Michael C. Soldner

(57) ABSTRACT

A medical device and associated method establish an occurrence of a premature atrial contraction. The device senses a ventricular signal. A control unit is configured to determine a metric of the ventricular signal during an interval following the premature atrial contraction and detect a change in cardiac stress tolerance in response to the determined metric.

22 Claims, 5 Drawing Sheets

DEVICE BASED CARDIAC MONITORING AND STRESS TEST

FIELD OF THE DISCLOSURE

The disclosure relates generally to medical devices and, in particular, to a medical device and associated method for assessing cardiac stress.

BACKGROUND

A cardiac stress test is performed to measure the response of the heart to exercise or drug-induced stress. A cardiac stress test is generally performed after a patient has experienced symptoms or when cardiac ischemia or other heart disease is suspected. However patients may develop a change in the cardiac substrate over time that may not manifest in recognizable symptoms for some time. A reduced tolerance to cardiac stress may go unrecognized until a patient experiences adverse symptoms or ischemic episodes, which could result in myocardial infarction, life-threatening arrhythmias or other serious consequences. Accordingly, there remains a need for a medical device system that enables early detection of reduced tolerance to cardiac stress that may be associated with pathological changes in the cardiac substrate, allowing early clinical intervention and improved patient care.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
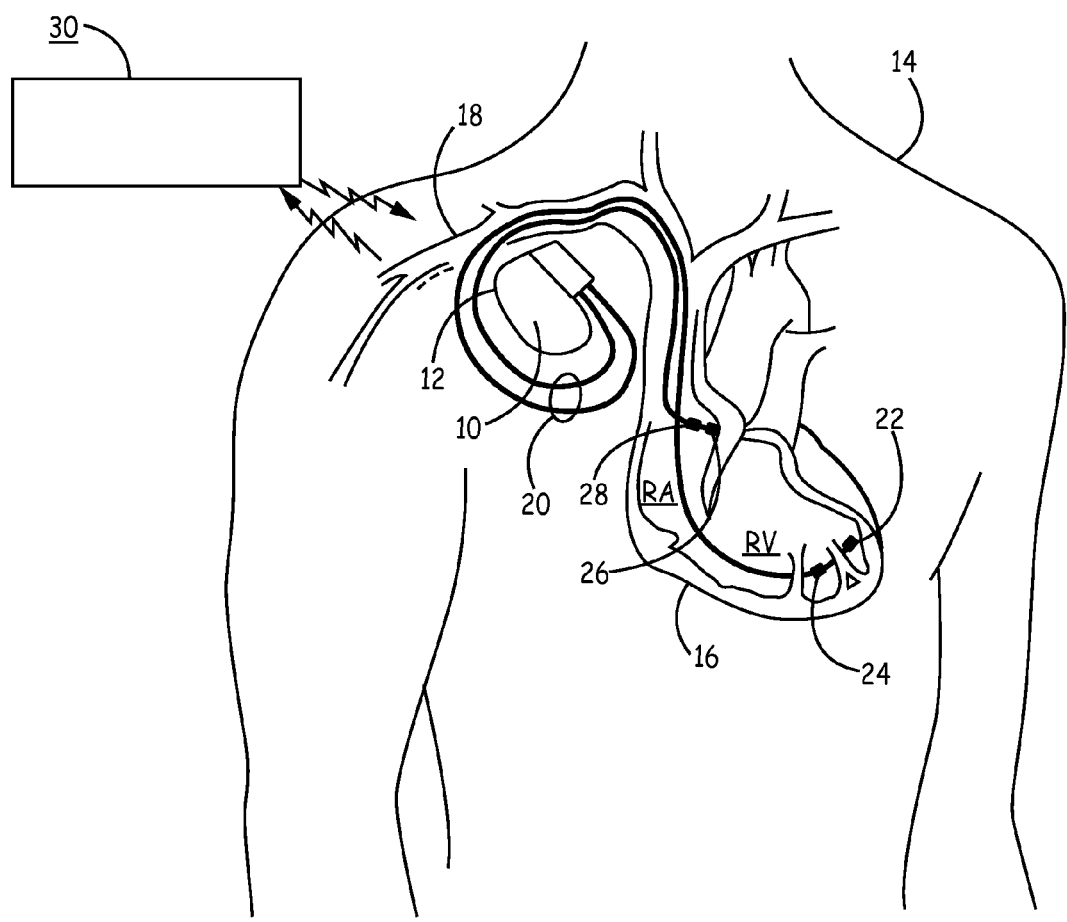
FIG. 1 is a schematic diagram of an implantable medical device system according to one embodiment.

FIG. 1 is a schematic diagram of an implantable medical device system according to one embodiment. System 8 is configured to perform device-based cardiac stress assessment by monitoring a ventricular response to a premature atrial contraction (PAC) conducted to the ventricles. It is hypothesized that a PAC induces stress to the heart because the ventricles have to contract sooner than normally scheduled. In a normal heart, this stress imposed on the ventricles by a PAC can be easily accommodated. However, in a heart with a diseased cardiac substrate, such as coronary artery disease or other ischemic disease, a ventricular response to a PAC may reveal an underlying disease state, which may be otherwise asymptomatic. PACs can be common in patients. By monitoring a post-PAC cardiac signal correlated to ventricular function, a stress assessment can be made to identify indicators of possible changes in the cardiac substrate over time. A monitored cardiac signal may include a ventricular ECG or EGM signal, ventricular or arterial pressure, a blood flow pattern (for assessing blood vessel stiffness), a signal correlated to an autonomic response, heart sounds or heart wall motion, for example. Changes in the post-PAC cardiac signal may be predictive of future adverse cardiac events and could be valuable to a clinician in selecting and managing cardiac disease therapies.

As illustrated in FIG. 1, a system 8 for assessing a cardiac stress response to PACs includes IMD 10 and an external device 30. IMD 10 is provided for sensing cardiac events (e.g. P-waves and R-waves) and delivering cardiac pacing pulses to the heart 16 of a patient 14. In the embodiment shown, IMD 10 is a dual chamber pacemaker and is coupled to one or more leads, collectively identified with reference numeral 20. Leads 20 are electrically coupled to the IMD 10 and extend into the patient's heart 16 via a vein 18. Leads 20 include electrodes 22 and 24 shown positioned in the patient's right ventricle (RV) and electrodes 26 and 28 positioned in the patient's right atrium (RA) for sensing EGM signals and pacing in the RV and RA, respectively.

In alternative embodiments, IMD 10 at least senses an atrial electrical signal, i.e. EGM or ECG, via intracardiac, epicardial, or subcutaneous leads for detecting intrinsic PACs and senses a cardiac signal correlated to ventricular function for obtaining a signal for assessing the ventricular response to a PAC conducted to the ventricles. IMD 10 may be embodied as a pacemaker, implantable cardioverter defibrillator (ICD), cardiac monitor, drug pump, or neurostimulator. When IMD 10 is embodied as an ICD, leads 20 may additionally carry high voltage coil electrodes used to deliver cardioversion and defibrillation shock pulses.

The leads 20 are used to acquire intracardiac EGM signals from the patient 14. IMD may be configured to deliver pacing pulses, which may include diagnostic pacing pulses for inducing PACs and/or therapeutic pacing pulses for delivering pacing therapies such as bradycardia pacing, anti-tachycardia pacing, or cardiac resynchronization therapy, or neuromodulation. A post-PAC ventricular response may be assessed following an intrinsically occurring PAC sensed by IMD 10 and/or following PACs induced using electrodes 26 and 28 to deliver a premature atrial pacing pulse. In various embodiments, a medical device system configured to perform device-based cardiac stress assessment using the techniques described herein may rely only on sensing intrinsic PACs for measuring a post-PAC ventricular response, only induced PACs which requires the capability of delivering premature atrial pacing pulses, or a combination of both.

IMD 10 may alternatively be configured as a subcutaneous device having sensing or pacing electrodes incorporated on the housing 12 of IMD 10 in which case transvenous leads 20 are not required. A subcutaneous device for performing cardiac stress assessments may be coupled to a lead tunneled subcutaneously or submuscularly for delivering transthoracic pacing pulses and/or sensing ECG signals. The techniques described herein can also be implemented in an external device, e.g. including patch electrodes and optionally another physiological sensor if desired, that can sense variable parameters as described herein for assessment of stress tolerance.

IMD circuitry and associated battery(ies) are housed within a sealed housing 12, which may itself be conductive so as to serve as an electrode for use as an indifferent electrode during pacing or sensing. As such, housing 12 is also referred to herein as "housing electrode" 12.

The embodiments described herein relate primarily to an IMD acquiring cardiac EGM signals and a cardiac signal correlated to ventricular signal which may be a ventricular EGM signal, or any of the other signals listed previously. The techniques disclosed herein, however, may be implemented in any implantable or external device used to acquire cardiac electrical signals (EGM or ECG signals) for detecting intrinsic PACs or delivering pacing pulses to induce PACs. The ventricular response to the PAC may be assessed from the EGM or ECG signal or from another physiological signal correlated to ventricular function.

The data relating to stress assessment accumulated by IMD 10 can be transmitted to an external device 30, which may be embodied as a programmer, e.g. used in a clinic or hospital to communicate with IMD 10 via wireless telemetry. External device 30 may alternatively be embodied as a computer, home monitor, or hand-held device including cell phones, smart phones or the like, enabled to communicate directly or indirectly with IMD 10 for retrieving data acquired by IMD 10.

External device 30 may be coupled to a remote patient monitoring system, such as Carelink®, available from Medtronic, Inc., Minneapolis, Minn., or a remote database that allows clinicians or other experts to access data retrieved from IMD 10 via external device 30. Reference is made to commonly-assigned U.S. Pat. No. 6,599,250 (Webb et al.), U.S. Pat. No. 6,442,433 (Linberg et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming, all of which patents are hereby incorporated herein by reference in their entirety. Remote patient management systems, such as the Carelink® Network (Medtronic, Inc., Minneapolis, Minn., USA) may be adapted to utilize the presently disclosed techniques to perform device-based cardiac stress testing.

Figure 2:
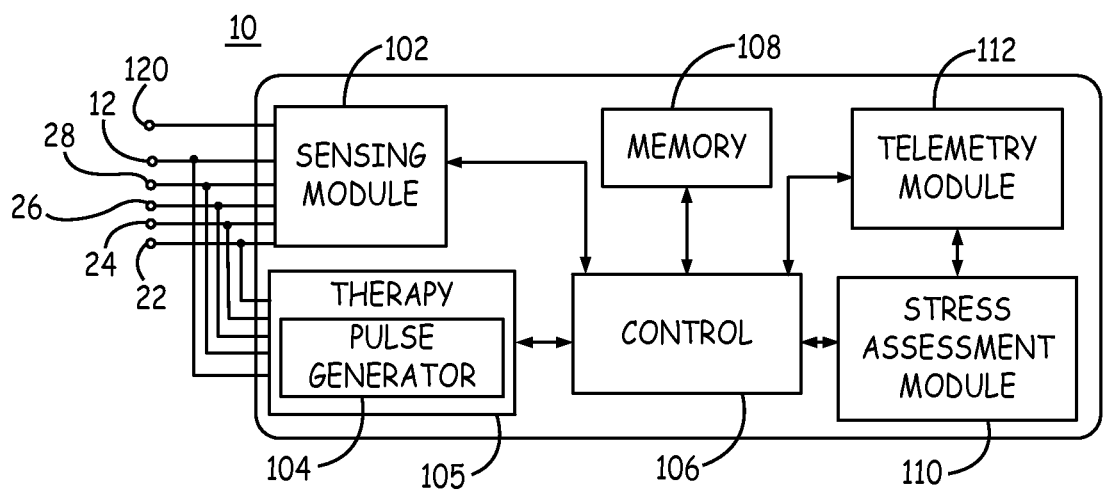
FIG. 2 is a functional block diagram of an IMD configured to perform a cardiac stress assessment in response to a premature atrial contraction according to one embodiment.

FIG. 2 is a functional block diagram of an IMD configured to perform a cardiac stress assessment according to one embodiment. IMD 10 includes a sensing module 102, a therapy delivery module 105 including a pulse generator 104, a control unit 106, memory 108, a stress assessment module 110 and a telemetry module 112. Sensing module 102 is coupled to electrodes 22, 24, 26 28 and housing electrode 12 (all shown in FIG. 1) for sensing cardiac EGM signals.

Sensing module 102 monitors cardiac electrical signals for sensing cardiac electrical signals attendant to the depolarization of myocardial tissue, e.g. P-waves and R-waves, from selected ones of electrodes 22, 24, 26, 28, and housing electrode 12 in order to monitor electrical activity of heart 16. Sensing module 102 may include a switch module to select which of the available electrodes are used to sense the cardiac electrical activity. The switch module may include a switch array, switch matrix, multiplexer, or any other type of switching device suitable to selectively couple electrodes to sensing module 102. In some examples, control 106 selects the electrodes to function as sense electrodes, or the sensing vector, via the switch module within sensing module 102.

Sensing module 102 may include multiple sensing channels, each of which may be selectively coupled to respective combinations of electrodes 22, 24, 26, 28, and housing electrode 12 to detect electrical activity of a particular chamber of heart 16, e.g. an atrial sensing channel and a ventricular sensing channel. Each sensing channel may comprise an amplifier that outputs an indication to control unit 106 in response to sensing of a cardiac depolarization, in the respective chamber of heart 16. In this manner, control unit 106 may receive sense event signals corresponding to the occurrence of R-waves and P-waves in the various chambers of heart 16. Sensing module 102 may further include digital signal processing circuitry for providing processor 106 with digitized EGM signals, which may be used to measure EGM signal features or for signal morphology analysis in some embodiments.

Sensing module 102 and control unit 106 are configured to sense atrial P-waves and identify PACs among the sensed P-waves. Detection of PACs by control unit 106 may include analyzing P-P intervals and/or cross-chamber intervals (P-R and/or R-P intervals), analyzing sensed event patterns, and analyzing P-wave morphology. In one embodiment, a PAC can be defined as sensed P-wave occurring at P-P interval that is at least 10-20% shorter than a previously occurring P-P interval or P-P interval average. Practice of the techniques described herein is not limited to a particular technique for detecting intrinsic PACs as any method for detecting PACs may be employed in the embodiments that utilize intrinsically-occurring PACs for assessing cardiac stress.

In some embodiments, a ventricular signal sensed for assessing the post-PAC response may include a ventricular EGM signal sensed by sensing module 102 using electrodes 22, 24 and/or housing electrode 12. The ventricular EGM signal may be received by stress assessment module 110 for computing a post-PAC metric of the signal.

A ventricular signal sensed for assessing the post-PAC response may additionally or alternatively include a non-EGM signal, which may be an impedance signal measured using electrodes 12 through 28 or other dedicated impedance measuring electrodes. Impedance signal measurements that are responsive to changes in ventricular volume may be correlated to a change in ejection fraction post-PAC which, in turn, may reflect a change in stress tolerance.

Other non-EGM signals that may be monitored for a stress assessment include an accelerometer signal, pressure signal, heart sound signal, tissue oxygenation signal, or any other physiological signal responsive to ventricular function or the status of the ventricular myocardial substrate and containing information correlated to ventricular ischemia or stress. In these embodiments, IMD 10 is coupled to a sensor 120 for sensing the corresponding non-EGM signal. Sensor 120 may be a lead-based sensor coupled to IMD 10, incorporated on or in housing 12, or a wireless sensor transmitting a physiological signal to IMD 10 via telemetry module 112. Since the operation of sensor 120 may only be required for obtaining a post-PAC ventricular signal, control unit 106 may enable sensor 120 to operate only when needed to conserve the longevity of the IMD battery (not shown) and reduce processing burden.

Sensing module 102 provides the ventricular signal acquired from sensor 120 to stress assessment module 110. Sensing module 102 may include various signal conditioning components such as an amplifier(s), filter(s), rectifier(s), and analog-to-digital convertor(s), as needed, for providing one or more ventricular signals to stress assessment module for computing a post-PAC metric correlated to ventricular stress.

Pulse generator 104 is coupled to electrodes 22, 24, 26, 28 and 12 for delivering pacing pulses to the patient's heart. In some embodiments, control unit 106 controls pulse generator 104 to deliver premature atrial pacing pulses according to a monitoring protocol, using electrodes 26 and 28 for example. A monitoring protocol, as described further below, may include inducing a PAC or a run of PACs periodically by delivering pacing pulses at a predetermined PAC interval or multiple predetermined PAC intervals. The predetermined PAC interval is selected to deliver pacing pulses for inducing a PAC earlier than the next expected intrinsic atrial depolarization.

Pulse generator 104 may additionally or alternatively be controlled by control unit 106 for delivering an electrical stimulation therapy, which may be a cardiac pacing therapy or a neurostimulation therapy. Therapy module 105 may be configured for delivering other types of therapies, such as drug delivery. Control unit 106 may control therapy module 105 to deliver or adjust a therapy in response to detecting a decreased (or increased) stress tolerance indicating a change in the ventricular myocardial substrate.

The control unit 106 may be embodied as a processor including any one or more of a microprocessor, a digital signal processor (DSP), an application specific integrated circuit (ASIC), a field-programmable gate array (FPGA), or equivalent discrete or integrated logic circuitry. In some examples, control unit 106 may include multiple components, such as any combination of one or more microprocessors, one or more controllers, one or more DSPs, one or more ASICs, or one or more FPGAs, as well as other discrete or integrated logic circuitry. The functions attributed to control unit 106 herein may be embodied as software, firmware, hardware or any combination thereof. Control unit 106 includes a therapy control unit that controls therapy module 105 to deliver a therapy to heart 16 according to a selected one or more therapy programs, which may be stored in memory 108.

In one example, stress assessment module 110 may, at least in part, be stored or encoded as instructions in memory 108 that are executed by control unit 106. Stress assessment module 110 is configured to receive a ventricular signal from sensing module 102 in response to a detected or induced PAC and determine a post-PAC metric from the ventricular signal. The post-PAC metric is evaluated to detect evidence of a decrease (or increase) in cardiac stress tolerance.

Memory 108 stores intervals, counters, or other data used by control unit 106 to control sensing module 102, pulse generator 104 and therapy module 105, and stress assessment module 110. Such data may include intervals and counters used by control unit 106 to control the delivery of pacing pulses to heart 16, such as PAC intervals for controlling the delivery of premature atrial pacing pulses for inducing PACs. Memory 108 also stores intervals for controlling cardiac sensing functions such as blanking intervals and refractory sensing intervals. Events (P-waves and R-waves) sensed by sensing module 102 may be identified based on their occurrence outside a blanking interval and inside or outside of a refractory sensing interval.

Memory 108 may store computer-readable instructions that, when executed by control unit 106, cause IMD 10, control unit 106 and stress assessment module 110 to perform various functions attributed throughout this disclosure to IMD 10. The computer-readable instructions may be encoded within memory 108. Memory 108 may comprise non-transitory computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media, with the sole exclusion being a transitory propagating signal.

Telemetry module 112 is used for transmitting data accumulated by IMD 10 wirelessly to external device 30 (FIG. 1). Examples of communication techniques used by IMD 10 include low frequency or radiofrequency (RF) telemetry, which may be an RF link established via Bluetooth, WiFi, or MICS. IMD 10 receives programming commands from external device 30 via telemetry module 112, which may include commands for performing a device-based stress test by inducing PACs according to a monitoring protocol. Telemetry module 112 may be controlled by control unit 106 for delivering a patient or clinician alert or notification to external device 30 in response to detecting a decrease in cardiac stress tolerance.

Figure 3:
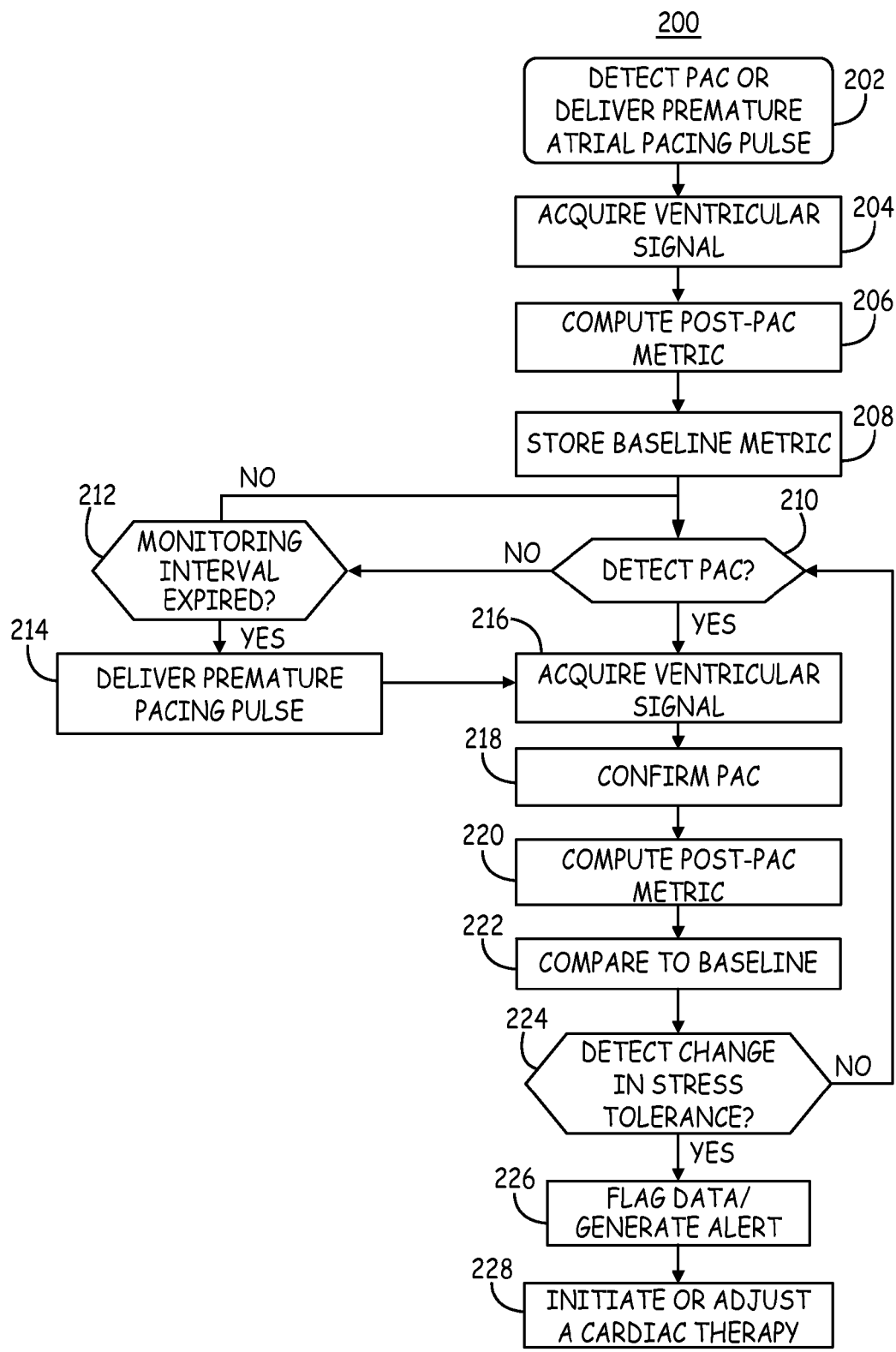
FIG. 3 is a flow chart of a method for assessing cardiac stress in a patient according to one embodiment.

FIG. 3 is a flow chart 200 of a method for assessing cardiac stress in a patient according to one embodiment. Flow chart 200 and other flow charts presented herein are intended to illustrate the functional operation of the medical device system, and should not be construed as reflective of a specific form of software or hardware necessary to practice the methods described. Methods described in conjunction with flow charts presented herein may be implemented in a non-transitory computer-readable medium that includes instructions for causing a programmable processor to carry out the methods described. A non-transitory computer-readable medium includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented as one or more software modules, which may be executed by themselves or in combination with other software.

At block 202, the occurrence of a PAC is established by either detecting an intrinsic PAC or delivering a premature atrial pacing pulse to induce a PAC. A premature pacing pulse is delivered at a PAC interval following a sensed P-wave that is shorter than a previously measured P-P interval by a predetermined amount. In this way, the premature pacing pulse is delivered prior to an expected intrinsic atrial depolarization. A previously measured P-P interval may be a P-P interval immediately prior to the premature pacing pulse delivery or an earlier P-P interval. A P-P interval used as a basis for timing a premature pacing pulse may be determined as a running average or other measurement of atrial intervals that excludes intervals corresponding to atrial arrhythmias such as atrial fibrillation or atrial flutter.

A ventricular signal is acquired at block 204. As described previously the ventricular signal may be a ventricular EGM signal, or a signal from a pressure sensor, accelerometer, impedance electrodes, optical sensor, acoustical sensor, or other sensor producing a signal containing information correlated to the ventricular response to stress.

In response to establishing a time of a PAC, a post-PAC metric is computed from the ventricular signal at block 206. In one example, a change in the ST segment of the ventricular EGM signal is determined as a post-PAC metric. Elevation or depression of the ST segment in response to a PAC may be evidence of an underlying ischemic change that is not observable during normal sinus rhythm beats. The unmasked ST elevation or depression following a PAC may suggest de novo ischemia, increasing severity of myocardial ischemia, or urgent myocardial ischemia warranting medical attention depending on the individual patient's cardiac health status. Accordingly, one post-PAC metric is the change or shift in ST segment amplitude (which may be measured as a difference from the EGM baseline signal) following the first sensed R-wave following a PAC as compared to the ST segment amplitude during a normal sinus beat.

In another example, a PAC may produce an oscillation of a pressure signal or blood flow signal. An amplitude or frequency of the oscillations of a pressure signal following a PAC may be measured as a post-PAC metric.

In various embodiments, determining a post-PAC metric may include determining an amplitude, slope, frequency, morphology or other feature of the acquired ventricular signal during a window of time following the PAC, which may be defined more specifically as a window of time following the first sensed R-wave after a PAC.

Initially, a baseline PAC response is stored at block 208 using the post-PAC metric. The baseline PAC response may be the post-PAC metric measured at block 206 or a difference between the metric and an analogous measurement made during a normal sinus rhythm beat. In other embodiments, a baseline measurement of the ventricular signal may be measured during a normal sinus rhythm beat (or multiple normal sinus rhythm beats), which is compared to post-PAC metrics to detect a decrease in stress tolerance.

After obtaining and storing a baseline metric, monitoring is performed to detect a change in stress tolerance. In some embodiments, the atrial EGM signal (or an ECG signal) is monitored for detecting PACs at block 210. If a PAC is detected, the ventricular signal is acquired at block 216. If a PAC is not detected within a maximum monitoring interval, as determined at block 212, a premature atrial pacing pulse is delivered at block 214, upon expiration of the maximum monitoring interval, to induce a PAC.

It is recognized that numerous monitoring protocols can be conceived. For example, determination of a post-PAC metric may be required daily, weekly, monthly or another periodic basis. The monitoring protocol may begin monitoring for a PAC at a scheduled time interval and upon detecting an intrinsic PAC, a post-PAC metric is measured. If the intrinsic PAC is not detected within a time limit, a premature pacing pulse is delivered. In other embodiments, the post-PAC metric may be measured every time a PAC is detected or for a portion of detected PACs, for example every $5^{th}$ PAC, every $10^{th}$ PAC, etc. A single PAC is one example of an event that may cause cardiac stress, however, other stress events may occur that will trigger a stress assessment such as a couplet of PACs or a short-run of atrial tachycardia. As such, detection of a PAC at block 210 is not limited to detection of a single isolated PAC but may more generally include a stress event associated with one or multiple early or fast atrial events such as a couplet or short run atrial tachycardia.

In other embodiments, the monitoring protocol does not wait for an intrinsic PAC to be detected and immediately delivers a premature pacing pulse (or a run of premature pacing pulses) at the end of a monitoring interval.

Upon either detecting a PAC or inducing a PAC, the ventricular signal is acquired at block 216. If the ventricular signal is acquired upon detecting a PAC, an optional step of confirming the detected PAC as a valid PAC may be performed at block 218 in some embodiments. For example, if the PAC is detected based on a short P-P interval, additional morphology analysis may be performed to verify the early sensed event is a P-wave and not a far-field R-wave, non-cardiac noise or other event.

At block 220, the post-PAC metric is computed from the ventricular signal. If the post-PAC metric is being computed subsequent to an intrinsically sensed PAC, the metric may be scaled or normalized by the intrinsic PAC interval to allow comparisons between metrics measured at somewhat different intrinsically-occurring PAC intervals. Alternatively, some intrinsic PACs may be rejected for performing stress assessment if the PAC interval is significantly different than a PAC interval used to establish a baseline measurement.

The post-PAC metric is compared to the stored baseline metric at block 222. If the post-PAC metric has changed by a threshold amount, which may be a percentage or other difference relative to the baseline, a change in stress tolerance is detected at block 224. A change in stress tolerance could be a decrease in stress tolerance indicating a worsening cardiac condition or an increase in stress tolerance indicating an improvement in a cardiac condition, possibly in response to a cardiac therapy.

If the post-PAC metric has not changed significantly from the baseline or does not cross a detection threshold, the process returns to block 210 to wait for the next intrinsic PAC detection or premature atrial pacing pulse delivery in accordance with the monitoring protocol schedule.

If a change in stress tolerance is detected at block 224, particularly a decrease in stress tolerance, a patient and/or clinician alert may be generated at block 226. The post-PAC metric and ventricular signal segment recording the post-PAC response may be stored and flagged for transmission to external device 30 for review by a clinician. IMD 10 may deliver or adjust a therapy in response to detecting a change in stress tolerance at block 228. If a decrease in stress tolerance is detected, a therapeutic measure can be initiated such as drug delivery, neuromodulation, preconditioning ventricular pacing, or other pacing therapy adjustment. If an improvement in stress tolerance is detected, a therapy may be stopped or decreased.

Figure 4:
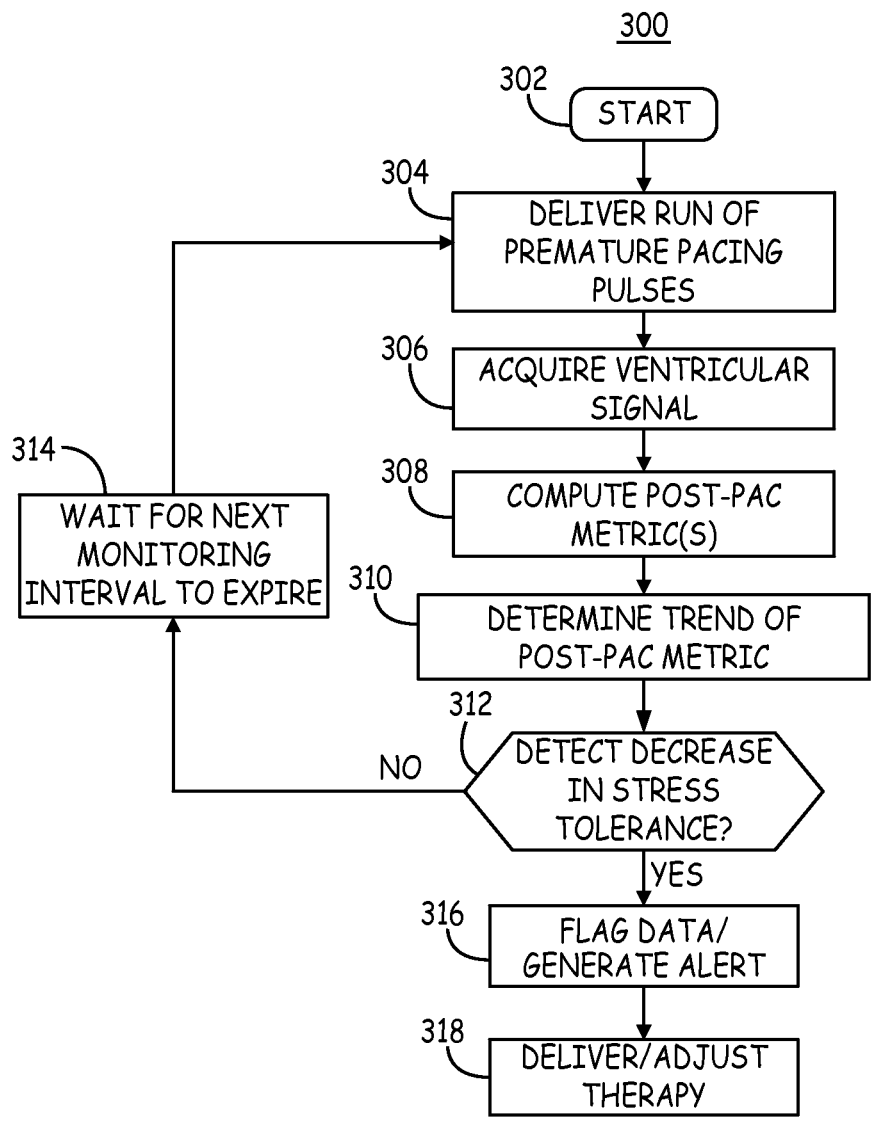
FIG. 4 is a flow chart of a method for performing device-based cardiac stress testing according to another embodiment.

FIG. 4 is a flow chart 300 of a method for performing device-based cardiac stress testing according to another embodiment. At block 302, a stress assessment is initiated. A stress assessment may be initiated at a scheduled time according to a monitoring protocol. Additionally or alternatively, a stress assessment can be initiated by the IMD automatically in response to another monitored parameter or event such as a change in heart rate or heart rate variability. For example, when the heart rate increases and/or heart rate variability decreases, suggesting an elevation of sympathetic activation, a stress assessment may give more meaningful results relating to cardiac condition or changes in myocardial substrate than at times of resting heart rate.

At block 304, a run of premature atrial pacing pulses is delivered. The run of premature atrial pacing pulses may be delivered consecutively or with intervening intrinsic beats. An individual run may include two or more pacing-induced PACs, and in some embodiments more than one run of PACs may be induced.

A number of factors may be varied within a run of premature pacing pulses or between runs of pacing pulses. The control parameters used by the control unit 106 to control the pulse generator 104 delivering the premature atrial pacing pulses may be adjusted during a run or between runs for causing an increase in cardiac stress within or between runs of pacing pulses. Control parameters that are adjusted may include, for example, a number of pulses within a run, the PAC interval, the time intervals or number of intrinsic beats between pacing-induced PACs (i.e. frequency of PACs within the run), and a number of runs of PACs delivered within a given monitoring episode.

The PAC interval is the interval between the premature pacing pulse and the immediately preceding intrinsic (or paced) P-wave. A longer PAC interval results in a less premature PAC, which may cause less stress to the ventricle than a more premature, earlier PAC, i.e. a shorter PAC interval.

By adjusting a pacing control parameter to cause an increase in the cardiac stress imposed on the heart within a monitoring episode, a determination can be made whether the stress tolerance is increasing, decreasing or staying the same between stress assessments. In one embodiment, premature pacing pulses are delivered to induce a sequence of PACs until a change in the post-PAC ventricular signal is detected, up to a predetermined maximum number of PACs. If a change in the ventricular signal is detected after fewer PACs compared to a previous stress assessment, a decrease in stress tolerance would be detected.

In another example, the PAC interval may be progressively decreased during a run of premature pacing pulses, up to a maximum prematurity. A determination may be made to determine at what PAC interval a change in the post-PAC metric is detected. A patient may tolerate a PAC occurring at a relatively long PAC interval, but be less tolerant of a PAC occurring at a short interval. A decreased tolerance to a PAC at a relatively long interval as measured by a greater change in the post-PAC metric compared to a previously measured post-PAC metric for the same PAC interval would indicate a worsening condition of the myocardial substrate.

At block 308, a post-PAC metric is computed from the ventricular signal for one or more of the induced PACs. For example, the metric may be computed for each induced PAC, only the last induced PAC, the first and the last induced PACs of the run of PACs or another subset of the run of PACs. When the post-PAC metric is computed for more than one of the induced PACs, a trend in the post-PAC metric within or between runs of PACs may be determined at block 310. For example, a trend may be determined between a first and last PAC within a run. In another example, a trend of the post-PAC metric for an nth one of the induced PACs may be compared to the post-PAC metric for the nth one of a previous run of PACs.

The trend of the post-PAC metrics is analyzed at block 312 to detect a decrease in stress tolerance. Changes in the trend over time (between monitoring episodes) may be measured for detecting a decrease (or increase) in stress tolerance. For example, if the trend indicates an increased change in the post-PAC metric for a fewer number of PACs within a run or a longer PAC interval compared to a previous stress assessment, a decrease in stress tolerance is detected at block 312. If no change in stress tolerance is detected, the process advances to block 314 to wait for the next monitoring interval to expire and the process then repeats by returning to block 302.

If a decrease in stress tolerance is detected, the data relating to the detection may be stored and flagged for review by a clinician. A patient and/or a clinician alert may be generated at block 316. Additionally or alternatively, a therapy may be delivered or adjusted by IMD 10 to alleviate an ischemic condition.

While block 312 indicates detecting a decrease in stress tolerance, i.e. a worsening condition of the myocardial substrate, it is contemplated that the techniques described in conjunction with FIG. 4 may also be used to detect a change in the stress tolerance indicative of an improvement in the myocardial substrate. If an improvement is detected, a therapy being delivered to alleviate an ischemic condition may be adjusted or stopped.

Figure 5:
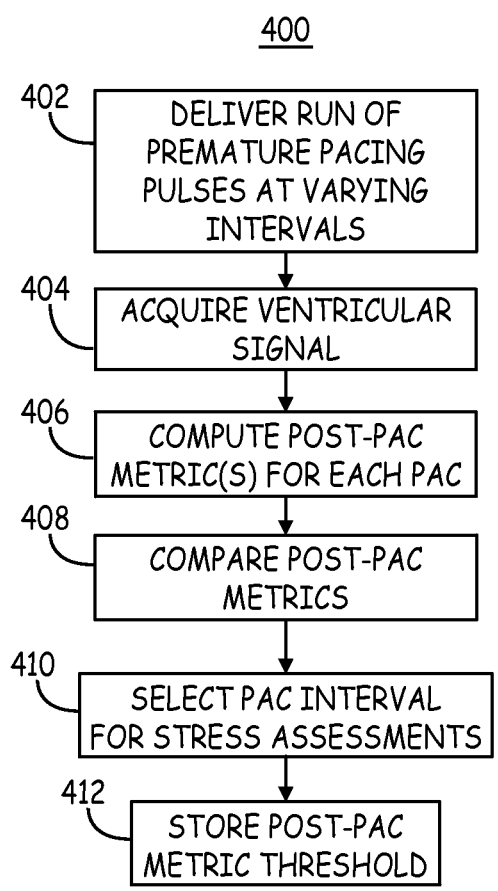
FIG. 5 is a flow chart a method for establishing a PAC interval used for performing a stress assessment.

FIG. 5 is a flow chart 400 of a method for establishing a PAC interval used for performing a stress assessment. At block 402, a run of premature pacing pulses are delivered at varying PAC intervals. The PAC intervals could vary from approximately 40% to 90% of a baseline P-P (or R-R interval).

At block 404, the ventricular signal is acquired and a post-PAC metric is computed for each PAC interval at block 406. The post-PAC metrics are compared at block 408 to establish a relationship between stress tolerance and the PAC interval. A 90% PAC interval may not generate a meaningful stress assessment result in many patients because the interval is too close to the normal P-P interval. A shorter PAC interval will be more likely to induce ventricular stress, yielding a meaningful result of the stress tolerance assessment. Thus, a relationship curve can be created by plotting or tabulating the PAC interval and the corresponding post-PAC metric over a range of PAC intervals.

At block 410, a PAC interval is selected for use during future stress assessments in response to the relationship curve. A PAC interval resulting in a measurable change in the post-PAC metric, for example at least an approximately 20% change in the post-PAC metric as compared to a baseline measurement or compared to the longest PAC interval tested, may be selected as the PAC interval used in subsequent stress assessments. If no change is measured over a range of PAC intervals, the shortest PAC interval may be selected for use in future stress assessments. The PAC interval is stored in memory 108 and may be used for delivering a single PAC or a run of PACs in subsequent stress assessments performed on a scheduled or triggered basis.

The value of the post-PAC metric at the selected PAC interval may be stored as a threshold for detecting a change in stress tolerance at block 412. A significant change in the post-PAC metric measured following an induced PAC at the selected PAC interval would be detected as a change in stress tolerance. For example if the post-PAC metric changes by more than at least 10% of the threshold value, a change in stress tolerance is detected. It is recognized that a detection threshold for detecting a change in stress tolerance may be dependent on the post-PAC measurement being made, the resolution of the measurement, clinician preference, individual patient need, or other factors.

Thus, a device and method for performing a device-based cardiac stress assessment have been presented in the foregoing description with reference to specific embodiments. It is appreciated that various modifications to the referenced embodiments may be made without departing from the scope of the disclosure as set forth in the following claims.

The invention claimed is:

1. A method for detecting change in cardiac stress tolerance in a medical device, comprising:
   establishing an occurrence of a premature atrial contraction;
   sensing a ventricular signal comprising an S-T segment subsequent to the established occurrence;
   determining a metric of the ventricular signal S-T segment during an interval following the premature atrial contraction; and
   detecting a change in cardiac stress tolerance in response to the determined metric.

2. The method of claim 1, wherein establishing an occurrence of the premature atrial contraction comprises sensing an intrinsic premature atrial contraction.

3. The method of claim 1, wherein establishing an occurrence of the premature atrial contraction comprises delivering a premature atrial pacing pulse.

4. The method of claim 3, wherein delivering the premature atrial pacing pulse comprises delivering a run of premature atrial pacing pulses.

5. The method of claim 1, wherein the metric of the ventricular signal ST segment is a change in ST segment amplitude.

6. A method for detecting change in cardiac stress tolerance in a medical device, comprising:
   establishing an occurrence of a premature atrial contraction by delivering a run of premature atrial pacing pulses;
   sensing a ventricular signal subsequent to the established occurrence;
   determining a metric of the ventricular signal during an interval following the premature atrial contraction;

adjusting a pacing control parameter controlling the run of premature atrial pacing pulses to cause increasing cardiac stress during the run;
determining a trend of the metric over the run; and
detecting a change in stress tolerance in response to the trend.

7. The method of claim 6, wherein adjusting the pacing control parameter comprises decreasing a pacing interval within the run.

8. The method of claim 7, further comprising detecting a decrease in stress tolerance in response to detecting a change in the metric at a relatively shorter pacing interval than a previously detected change.

9. The method of claim 6, further comprising
determining a number of premature atrial pacing pulses in the run required to cause a change in the metric; and
detecting the change in the stress tolerance in response to determining the number.

10. The method of claim 6, wherein the ventricular signal comprises one of an EGM signal, an ECG signal, a pressure signal, a heart sound signal, an oxygen saturation signal, and an accelerometer signal.

11. The method of claim 6, further comprising:
varying a pacing interval during the run of premature atrial pacing pulses;
computing the metric of the ventricular signal for each of the premature atrial pacing pulses;
establishing a relationship between the varied pacing interval and the metric; and
selecting a pacing interval for inducing a premature atrial pacing pulse in response to the established relationship,
wherein establishing the time of the premature atrial contraction comprises delivering a premature atrial pacing pulse at the selected pacing interval.

12. A medical device, comprising:
a sensing module for sensing an atrial signal and a ventricular signal comprising an ST segment; and
a control unit configured to establish an occurrence of a premature atrial contraction, determine a metric of the ventricular signal ST segment during an interval following the premature atrial contraction, and determine a change in cardiac stress tolerance in response to the determined metric.

13. The device of claim 12, wherein establishing the occurrence of the premature atrial contraction comprises sensing an intrinsic premature atrial contraction from the atrial signal.

14. The device of claim 12, further comprising a pulse generator,
wherein establishing the occurrence of the premature atrial contraction comprises controlling the pulse generator to deliver a premature atrial pacing pulse.

15. The device of claim 14, wherein delivering the premature atrial pacing pulse comprises delivering a run of premature atrial pacing pulses.

16. A medical device, comprising:
a sensing module for sensing an atrial signal and a ventricular signal;
a pulse generator; and
a control unit configured to:
establish an occurrence of a premature atrial contraction by controlling the pulse generator to deliver a run of premature atrial pacing pulses,
adjust a pacing control parameter controlling the run of premature atrial pacing pulses to cause increasing cardiac stress during the run,
determine a metric of the ventricular signal during an interval following the premature atrial contraction,
determine a trend of the metric over the run, and
detect a change in stress tolerance in response to the trend.

17. The device of claim 16, wherein adjusting the pacing control parameter comprises adjusting a pacing interval within the run.

18. The device of claim 17, wherein the control unit is configured to detect a decrease in stress tolerance in response to detecting a change in the metric at a relatively longer pacing interval than a previously detected change.

19. The device of claim 16, wherein the control unit is configured to:
determine a number of premature atrial pacing pulses in the run required to cause a change in the metric; and
detect the change in the stress tolerance in response to determining the number.

20. The device of claim 16, wherein the ventricular signal comprises one of an EGM signal, and ECG signal, a pressure signal, a heart sound signal, an oxygen saturation signal, and an accelerometer signal.

21. The device of claim 16, further comprising,
the control unit configured to:
control the pulse generator to vary a pacing interval during the run of premature atrial pacing pulses,
compute the metric of the ventricular signal for each of the premature atrial pacing pulses,
establish a relationship between the varied pacing interval and the metric, and
select a pacing interval for inducing a premature atrial pacing pulse in response to the established relationship, wherein establishing the time of the premature atrial contraction comprises controlling the pulse generator to deliver a premature atrial pacing pulse at the selected pacing interval.

22. A non-transitory computer-readable medium comprising instructions for causing a processor of a medical device system to perform a method, the method comprising:
establishing an occurrence of a premature atrial contraction;
sensing a ventricular signal comprising an ST segment subsequent to the established occurrence;
determining a metric of the ventricular signal ST segment during an interval following the premature atrial contraction; and
detecting a change in cardiac stress tolerance in response to the determined metric.

\* \* \* \* \*